US006255049B1

(12) United States Patent
Fisher

(10) Patent No.: US 6,255,049 B1
(45) Date of Patent: *Jul. 3, 2001

(54) DETECTION OF METASTATIC CANCER CELLS USING PCTA-1

(75) Inventor: Paul B. Fisher, Scarsdale, NY (US)

(73) Assignee: The Trustees of Columbia University in the City of New York, New York, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/032,311

(22) Filed: Feb. 27, 1998

(51) Int. Cl.[7] ............................. C12Q 1/68; C12P 19/34; C07H 21/04

(52) U.S. Cl. ........................... 435/6; 435/91.2; 435/91.5; 435/91.51; 536/23.5; 536/24.31; 536/24.33

(58) Field of Search ............................ 435/6, 91.1, 91.2, 435/91.5, 91.51; 536/24.3, 24.31, 24.33, 23.5

(56) References Cited

FOREIGN PATENT DOCUMENTS 96 21671    7/1996   (WO).

OTHER PUBLICATIONS

Fisher, P., B., (1995) "A new technology for preparig monoclonal antibodies to molecules expressed on the cell surface", *Pharmaceutical Tech.* 19(9):42–48, (Exhibit 2).

Gronberg, H., et al., (1997) "Early age at diagnosis in families provided evidence of linkage to the hereditary prostate cancer locus (HPCI) on chromosome 1", *Cancer Res.* 57:4707–4709, (Exhibit 3).

Raz, A. and Lotan, R., (1987) "Endogenous galactoside–binding lectins: a new class of functional tumor or cell surface molecules related to metastasis", *Cancer Metastasis Rev*, 6:433–452, (Exhibit 4)

Shen, R., et al., (1994) "Surface epitope masking: a strategy for the development of monoclonal antibodies specific for molecules expressed on the cell surface", *J. Natl. Cancer Inst.* 86:91–98, (Exhibit 5).

Smith, J.R., et al., (1996) "Major susceptibility locus for prostate cancer on chromosome 1 suggested by a genome–wide search", *Science* 274:1371–1375, (Exhibit 6).

Su, Z–Z, et al., (1996) "Surface–epitope masking and expression cloning identifies the human prostate carcinoma tumor antigen gene PCTA–1 a member of the galectin gene family", *Proc. Natl. Acad. Sci. U.S.A.* 93:7252–7257, (Exhibit 7).

(List continued on next page.)

Primary Examiner—Carla J. Myers
Assistant Examiner—Diana Johanssen
(74) Attorney, Agent, or Firm—John P. White; Cooper & Dunham LLP

(57) ABSTRACT

This invention provides a method of detecting cancer metastatic cells in a subject, comprising: a) obtaining a nucleic acid sample from the subject's blood; b) amplifying nucleic acid encoding the product of prostate carcinoma tumor antigen gene-1; and c) detecting the presence of nucleic acid encoding the product of the prostate carcinoma tumor antigen gene-1, thereby detecting cancer metastatic cells in a subject. This invention also provides the above-described methods, wherein the method of amplification is PCR. This invention further provides the above-described methods, wherein the primers are 5'-AAGCTGACGCCTCATTTGCA-3' SEQ ID NO: 1 and 5'-AACCACCAATGGAACTGGGT-3' SEQ ID NO: 2. This invention also provides the above-described methods, wherein the primers are 5'-AATGGCTTCTGTGATACT-3' SEQ ID NO: 3 and 5'-GGCTATAAGTGTTGCTGC-3'SEQ ID NO: 4.

4 Claims, 9 Drawing Sheets

OTHER PUBLICATIONS

Su, Zao-Zhong, Goldstein, Neil I. and Fisher, Paul B., (1998) "Antisense inhibition of the PTI-1 oncogene reverses cancer phenotypes", *Proc. Natl. Acad. Sci. USA* 95:1–6, (Exhibit 8); and.

Sun, Y., et al., (1997) "Human prostatic carcinoma oncogene PTI-1 is expressed in human tumor cell lines and prostate carcinoma patient blood samples", *Cancer Res.* 57:18–23, (Exhibit 9).

Sokoloff, M.H. et al. Quantitative PCR does not improve preoperative prostate cancer staging: a clinicopathological molecular analysis of 121 patients. J. Urology 156:1560–1566, 1996.*

Heid, C.A. et al. Real time quantitative PCR. Genome Research 6:986–994, 1996.*

Hadari, Y.R. et al. Galectin-8. J. Biol. Chem. 270(7):3447–3453, 1995.*

Hadari, Y.R. Galectin-8: on the road from structure to function. Trends Glycos. Glycotech. 9(45):103–112, Jan. 1997.*

Caulet-Maugendre, S. et al. Galectin-8 expression in squamous cell metaplasia of the bronchial epithelium in squamous cell cancer and benign processes. Modern Pathology 11(1):A172, Jan. 1998.*

Sokoloff, M. et al. Super-sensitive and quantitative PCR: an innovative technique for staging and monitoring prostate cancer. J. Urol. 153(4) Suppl:294A, 1995.*

* cited by examiner

SEQUENCE LISTING

<160> NUMBER OF SEQ ID NOS: 6

<210> SEQ ID NO: 1
<211> LENGTH: 20
<212> TYPE: DNA

```
<213> ORGANISM: Artificial Sequence
<220> FEATURE:
<223> OTHER INFORMATION: Description of Artificial Sequence:
      OLIGONUCLEOTIDE PRIMER

<400> SEQUENCE: 1
aagctgacgc ctcatttgca                                              20

<210> SEQ ID NO: 2
<211> LENGTH: 20
<212> TYPE: DNA
<213> ORGANISM: Artificial Sequence
<220> FEATURE:
<223> OTHER INFORMATION: Description of Artificial Sequence:
      OLIGONUCLEOTIDE PRIMER

<400> SEQUENCE: 2
aaccaccaat ggaactgggt                                              20

<210> SEQ ID NO: 3
<211> LENGTH: 18
<212> TYPE: DNA
<213> ORGANISM: Artificial Sequence
<220> FEATURE:
<223> OTHER INFORMATION: Description of Artificial Sequence:
      OLIGONUCLEOTIDE PRIMER

<400> SEQUENCE: 3
aatggcttct gtgatact                                                18

<210> SEQ ID NO: 4
<211> LENGTH: 18
<212> TYPE: DNA
<213> ORGANISM: Artificial Sequence
<220> FEATURE:
<223> OTHER INFORMATION: Description of Artificial Sequence:
      OLIGONUCLEOTIDE PRIMER

<400> SEQUENCE: 4
ggctataagt gttgctgc                                                18

<210> SEQ ID NO: 5
<211> LENGTH: 21
<212> TYPE: DNA
<213> ORGANISM: Artificial Sequence
<220> FEATURE:
<223> OTHER INFORMATION: Description of Artificial Sequence:
      OLIGONUCLEOTIDE PRIMER

<400> SEQUENCE: 5
tcttactcct tggaggccat g                                            21

<210> SEQ ID NO: 6
<211> LENGTH: 21
<212> TYPE: DNA
<213> ORGANISM: Artificial Sequence
<220> FEATURE:
<223> OTHER INFORMATION: Description of Artificial Sequence:
      OLIGONUCLEOTIDE PRIMER

<400> SEQUENCE: 6
cgtcttcacc accatggaga a                                            21
```

DETECTION OF METASTATIC CANCER CELLS USING PCTA-1

The invention disclosed herein was made with Government support under National Cancer Institute Grant Nos. CA35675 and CA21124 from the Department of Health and Human Services Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains.

BACKGROUND OF THE INVENTION

Adenocarcinoma of the prostate is the most common internal cancer of men in the United States and the second most frequent cause of cancer death (1). Identification of immunological and genetic reagents displaying specificity for prostate carcinoma versus normal prostate and BPH will be of immense value for the accurate diagnosis and possibly for the therapy of prostate cancer (2–6). Additionally, immunological reagents that can detect and bind to TAAs on the surface of prostate carcinoma cells, and that display limited expression on normal prostate and BPH tissue, may also prove of particular benefit for the detection and ultimately, therapy of prostate cancer (4,7,8).

Two novel approaches have been developed for defining the molecular and immunological basis of human cancer. One approach, the REXCS (2,3), permits the identification of putative oncogenic elements in human cancer DNAs. RExCS involves cotransfection of high molecular weight human tumor DNA in combination with a selectable antibiotic resistance gene into a new DNA acceptor cell line, CREF-Trans 6, selecting antibiotic resistant cells, injecting these cells into nude mice, and establishing cell cultures from tumors developing in athymic nude mice (2,3). Tumor-derived cell lines are then used to identify the putative human oncogenes, using approaches such as differential RNA display, that have been transferred from the human cancer cells into CREF-Trans 6 (3). Another methodology, SEM (7,8), results in the efficient and selective production of monoclonal antibodies reacting with tumor associated antigens present on the surface of human cancer cells (4,7,8). This procedure involves immunological subtraction based on the selective blocking of surface antigens on genetically altered cells (referred to as a "tester") with high titer polyclonal antibodies produced against untransfected parental cells (referred to as a "driver") This is followed by the production of hybridomas secreting MAbs that react with defined as well as uncharacterized cell surface expressed molecules (7,8).

Using SEM in combination with RExCS, prostate carcinoma (Pro 1.5) MAbs have been developed that react with TAAs expressed on human prostate cancer cell lines and patient-derived carcinomas (4,7,8). Addition of the Pro 1.5 MAb to nude mice containing human prostate cancer xenografts suppressed tumor growth and cancer progression. Screening a human LNCaP prostate cancer cDNA expression library with the Pro 1.5 MAb identified PCTA-1, a gene that encodes a novel galactose binding lectin, designated galectin-8HT (7). PCTA-1 was previously described in International Application No. PCT/US96/00307, filed Jan. 11, 1996, and published on Jul. 18, 1996 under International Publication No. WO 96/21671, which is herein incorporated by reference.

Using primer pairs corresponding to the 3' untranslated (UTR) region, RT-PCR detected PCTA-1 expression in prostatic carcinomas and PIN, but not in histologically confirmed normal prostate or BPH (7). Although further studies are necessary using a larger number of patient samples, these provocative results suggest that the Pro series of murine MAbs and the PCTA-1 gene should have direct diagnostic applications for human prostate cancer. Moreover, if the Pro MAbs show specificity toward prostate cancer, appropriately modified Pro MAbs, including chimerized and humanized versions of this MAb, may have therapeutic potential in patients with primary and metastatic prostate cancer.

PCTA-1 encodes a predicted protein structurally related to the S-type lectins (galectin) gene family (7). The galectins display wide tissue distribution, developmental regulation and differential expression levels in specific tissues, supporting the hypothesis that they contribute to many physiologically important processes in mammalian cells (9,10). Of direct relevance to cancer is the finding that the galectins, as well as the selectin subgroup of C-type lectins, mediate both cell-cell and cell-matrix interactions (10,11). These associations are critical elements in mediating the metastatic spread of tumor cells (12,13).

SUMMARY OF THE INVENTION

This invention provides a method of detecting cancer metastatic cells in a subject, comprising: a) obtaining a nucleic acid sample from the subject's blood; b) amplifying nucleic acid encoding the product of prostate carcinoma tumor antigen gene-1; and c) detecting the presence of nucleic acid encoding the product of the prostate carcinoma tumor antigen gene-1, thereby detecting cancer metastatic cells in a subject.

This invention also provides a method of determining the stage of cancer in a subject, comprising: a) obtaining a nucleic acid sample from the subject's blood; b) amplifying the nucleic acid encoding the product of prostate carcinoma tumor antigen gene-1; and c) quantifying the levels of RNA encoding the product of prostate carcinoma tumor antigen gene-1, thereby determining the stage of cancer in a subject.

This invention also provides the above-described methods, wherein the method of amplification is PCR.

Further, this invention provides the above-described methods, wherein the one of the primers is 5'-AAGCTGACGCCTCATTTGCA-3' SEQ ID NO:1.

This invention also provides the above-described methods, wherein the one of the primers is 5'-AACCACCAATGGAACTGGGT-3' SEQ ID NO:2.

This invention further provides the above-described methods, wherein the primers are 5'-AAGCTGACGCCTCATTTGCA-3' SEQ ID NO:1 and 5'-AACCACCAATGGAACTGGGT-3' SEQ ID NO:2.

In addition, this invention provides the above-described methods, wherein the one of the primers is 5'-AATGGCTTCTGTGATACT-3' SEQ ID NO:3.

Further, this invention provides the above-described methods, wherein the one of the primers is 5'-GGCTATAAGTGTTGCTGC-3' SEQ ID NO:4.

This invention also provides the above-described methods, wherein the primers are 5'-AATGGCTTCTGTGATACT-3' SEQ ID NO:3 and 5'-GGCTATAAGTGTTGCTGC-3' SEQ ID NO:4.

This invention also provides a method of detecting prostate cancer metastasis in a subject, comprising: a) obtaining a nucleic acid sample from the subject's blood; and b) applying a labeled probe that specifically hybridizes to the nucleic acid encoding the product of the prostate carcinoma tumor antigen gene-1, wherein the labeled probe produces a signal for detection and said signal amplifies detection of the probe.

This invention further provides the above-described methods, wherein the labeled probe comprises an enzyme that produces a detectable product, thereby amplifying detection of the probe.

BRIEF DESCRIPTION OF THE FIGURES

FIG. 1A Northern blotting analysis of PCTA-1 expression in cell lines and patient tissue samples. Lane designation: (1) CREF-Trans 6; (2) NHPE (passage #8); (3) CREF-Trans 6:4 NMT; (4) PC-3; (5) DU-145; (6) LNCaP; (7 & 8) two normal prostate tissue samples; (9,10,11 & 12) four prostate carcinoma tissue samples.

FIG. 1B RNase protection assay of PCTA-1 expression in cell lines. Protected 411 nt fragment is generated in PCTA-1 expressing CREF-Trans 6:4 NMT, LNCaP, DU-145 and PC-3 cells.

FIG. 1C RNase protection assay of PCTA-1 expression in tissue samples. Lane designation: (1, 2, 3 & 4) four prostate carcinoma tissue samples ; (5) a normal prostate tissue sample; (6) a PIN tissue sample; (7 & 8) two BPH tissue samples.

FIG. 2A RT-PCR analysis of PCTA-1 and GAPDH expression in normal prostate, BPH, PIN and prostate carcinoma tissues. Lane designation: (1) CREF-Trans 6; (2) CREF-Trans 6:4 NMT; (3) normal prostate; (4) low grade PIN; (5 to 8) BPH; (9) normal prostate; (10) focal PIN; (11) low grade PIN; (12 & 13) BPH; (14) PIN +10–15% tumor; (15) PIN +5% tumor; (16) adenocarcinoma (5–10% tumor); (17) adenocarcinoma (20% tumor).

FIG. 2B RT-PCR of PCTA-1 and GAPDH expression in CREF-Trans 6:4 NMT cells diluted with CREF-Trans 6 cells. The PCR-amplified products generated using a PCTA-1 3' UTR or a GAPDH primer pair (4) were blotted on nylon membranes and probed with a $^{32}$P-labeled DNA fragment of PCTA-1 or GAPDH, respectively. Similar results were obtained when DU-145 or LNCaP cells were diluted with CREF-Trans 6 cells.

FIG. 3A Samples in (A) include: 1 normal male; 7 stage D2 patients; 3 stage D1 patients; 1 stage D0 patient; and 1 stage C patient.

FIG. 3B Samples in (B) include: 1 normal male; 1 normal female; 4 stage D2 patients; 2 D1 patients; 2 D0 patients; DU-145; CREF-Trans 6:4 NMT (NMT); and CREF-Trans 6 (CREF).

DETAILED DESCRIPTION OF THE INVENTION

Figure 1A:
FIGS. 1A, 1B, and 1C Northern blotting and RNase protection assays detect PCTA-1 expression in prostate carcinoma cell lines and prostate carcinoma patient tissues.

This invention provides a method of detecting cancer metastatic cells in a subject, comprising: a) obtaining a nucleic acid sample from the subject's blood; b) amplifying nucleic acid encoding the product of prostate carcinoma tumor antigen gene-1; and c) detecting the presence of nucleic acid encoding the product of the prostate carcinoma tumor antigen gene-1, thereby detecting cancer metastatic cells in a subject.

This invention also provides a method of determining the stage of cancer in a subject, comprising: a) obtaining a nucleic acid sample from the subject's blood; b) amplifying the nucleic acid encoding the product of prostate carcinoma tumor antigen gene-1; and c) quantifying the levels of RNA encoding the product of prostate carcinoma tumor antigen gene-1, thereby determining the stage of cancer in a subject.

This invention provides a method of detecting prostate cancer metastasis in a subject, comprising: a) obtaining a nucleic acid sample from the subject's blood; b) amplifying nucleic acid encoding the product of prostate carcinoma tumor antigen gene-1; and c) detecting the presence of nucleic acid encoding the product of the prostate carcinoma tumor antigen gene-1, thereby detecting prostate cancer metastasis in a subject.

This invention provides a method of detecting breast cancer metastasis in a subject, comprising: a) obtaining a nucleic acid sample from the subject's blood; b) amplifying nucleic acid encoding the product of prostate carcinoma tumor antigen gene-1; and c) detecting the presence of nucleic acid encoding the product of the prostate carcinoma tumor antigen gene-1, thereby detecting breast cancer metastasis in a subject.

This invention provides a method of detecting colon cancer metastasis in a subject, comprising: a) obtaining a nucleic acid sample from the subject's blood; b) amplifying nucleic acid encoding the product of prostate carcinoma tumor antigen gene-1; and c) detecting the presence of nucleic acid encoding the product of the prostate carcinoma tumor antigen gene-1, thereby detecting colon cancer metastasis in a subject.

This invention provides a method of detecting lung cancer metastasis in a subject, comprising: a) obtaining a nucleic acid sample from the subject's blood; b) amplifying nucleic acid encoding the product of prostate carcinoma tumor antigen gene-1; and c) detecting the presence of nucleic acid encoding the product of the prostate carcinoma tumor antigen gene-1, thereby detecting lung cancer metastasis in a subject.

Methods of nucleic acid amplification include polymerase chain reaction (PCR) and rolling circle replication.

A basic description of nucleic acid amplification is described in Mullis, U.S. Pat. No. 4,683,202, which is incorporated herein by reference. The amplification reaction uses a template nucleic acid contained in a sample, two primer sequences and inducing agents. The extension product of one primer when hybridized to the second primer becomes a template for the production of a complementary extension product and vice versa, and the process is repeated as often as is necessary to produce a detectable amount of the sequence.

The inducing agent may be any compound or system which will function to accomplish the synthesis of primer extension products, including enzymes. Suitable enzymes for this purpose include, for example, E.coli DNA polymerase I, thermostable Taq DNA polymerase, Klenow fragment of E.coli DNA polymerase I, T4 DNA polymerase, other available DNA polymerases, reverse transcriptase and other enzymes which will facilitate combination of the nucleotides in the proper manner to form amplification products. The oligonucleotide primers can be synthesized by automated instruments sold by a variety of manufacturers or can be commercially prepared based upon the nucleic acid sequence of this invention.

The expression of prostate carcinoma tumor antigen gene-1 (PCTA-1) is specific to cancer. PCTA-1 is encoded by a gene located at 1q42–43.

This invention also provides a method of determining the stage of prostate cancer in a subject, comprising: a) obtaining a nucleic acid sample from the subject's blood; b) amplifying the nucleic acid encoding the product of prostate carcinoma tumor antigen gene-1; and c) quantifying the levels of RNA encoding the product of prostate carcinoma tumor antigen gene-1, thereby determining the stage of prostate cancer in a subject.

This invention also provides a method of determining the stage of colon cancer in a subject, comprising: a) obtaining a nucleic acid sample from the subject's blood; b) amplifying the nucleic acid encoding the product of prostate carcinoma tumor antigen gene-1; and c) quantifying the levels of RNA encoding the product of prostate carcinoma tumor antigen gene-1, thereby determining the stage of colon cancer in a subject.

This invention also provides a method of determining the stage of lung cancer in a subject, comprising: a) obtaining a nucleic acid sample from the subject's blood; b) amplifying the nucleic acid encoding the product of prostate carcinoma tumor antigen gene-1; and c) quantifying the levels of RNA encoding the product of prostate carcinoma tumor antigen gene-1, thereby determining the stage of lung cancer in a subject.

This invention also provides a method of determining the stage of breast cancer in a subject, comprising: a) obtaining a nucleic acid sample from the subject's blood; b) amplifying the nucleic acid encoding the product of prostate carcinoma tumor antigen gene-1; and c) quantifying the levels of RNA encoding the product of prostate carcinoma tumor antigen gene-1, thereby determining the stage of breast cancer in a subject.

As used herein, the stage of cancer refers to the progression of cancer both before, during, and after the beginnings of metastasis. It should be noted that the stage of cancer as used herein does not refer to the anatomically recognizable stages of progression as the molecular based methodology disclosed herein is distinct and more sensitive than anatomical methods of staging. In an embodiment, increased levels of metastasis are indicative of further stages of cancer.

This invention further provides the above-described methods, wherein the nucleic acid sample comprises total RNA.

This invention also provides the above-described methods, wherein the method of detection comprises using a labeled probe that specifically hybridizes to nucleic acid encoding the product of prostate carcinoma tumor antigen gene-1.

Probes may be labeled by any and all detectable means. Probe labeling methods include radioactivity, fluoresence, and enzyme-linked assays.

In addition, this invention provides the above-described methods, wherein the probe is radioactively labeled. $^{32}$p-labeled nucleic acid is one example of a radioactively labeled probe.

This invention also provides the above-described methods, wherein the method of amplification is PCR.

In an embodiment, appropriate PCR primers include but are not limited to 5'-AAGCTGACGCCTCATTTGCA-3' SEQ ID NO:1.

In an embodiment, appropriate PCR primers include but are not limited to 5'-AACCACCAATGGAACTGGGT-3' SEQ ID NO:2.

In another embodiment, appropriate PCR primers include but are not limited to 5'-AAGCTGACGCCTCATTTGCA-3' SEQ ID NO:1 and 5'-AACCACCAATGGAACTGGGT-3' SEQ ID NO:2.

In an embodiment, appropriate PCR primers include but are not limited to 5'-AATGGCTTCTGTGATACT-3'SEQ ID NO:3.

In another embodiment, appropriate PCR primers include but are not limited to 5'-GGCTATAAGTGTTGCTGC-3' SEQ ID NO:4.

In a further embodiment, appropriate PCR primers include but are not limited to 5'-AATGGCTTCTGTGATACT-3' SEQ ID NO:3 and 5'-GGCTATAAGTGTTGCTGC-3' SEQ ID NO:4.

This invention further provides the above-described methods, wherein the nucleic acid sample obtained from the subject's blood is total cellular RNA and the total cellular RNA is reverse-transcribed to cDNA before amplification.

This invention further provides the above-described methods, wherein the quantifying of step (c) comprises comparing strength of the hybridization signal for nucleic acid encoding the product of the prostate carcinoma tumor antigen gene-1 against the strength of the hybridization signal for a control nucleic acid.

This invention also provides the above-described methods, wherein the control nucleic acid encodes GAPDH.

In addition, this invention provides a method of detecting prostate cancer metastatic cells in a subject, comprising: a) obtaining a nucleic acid sample from the subject's blood; b) reverse transcribing the RNA to produce cDNA; c) amplifying the cDNA to the RNA encoding the product of prostate carcinoma tumor antigen gene-1; and d) detecting the presence of the cDNA to the RNA encoding the product of the prostate carcinoma tumor antigen gene-1, thereby detecting prostate cancer metastatic cells in a subject.

This invention also provides a method of detecting cancer metastasis in a subject, comprising: a) obtaining a nucleic acid sample from the subject's blood; and b) applying a labeled probe that specifically hybridizes to the nucleic acid encoding the product of the prostate carcinoma tumor antigen gene-1, wherein the labeled probe produces a signal for detection and said signal amplifies detection of the probe.

This invention also provides a method of detecting prostate cancer metastasis in a subject, comprising: a) obtaining a nucleic acid sample from the subject's blood; and b) applying a labeled probe that specifically hybridizes to the nucleic acid encoding the product of the prostate carcinoma tumor antigen gene-1, wherein the labeled probe produces a signal for detection and said signal amplifies detection of the probe.

Probes that produce signals that amplify detection of the probe include: radioactively labeled probes, enzyme-linked probes, and certain forms of antibody-linked and/or antigen-linked probes. Radioactive and enzyme-linked probes produce increasing amounts of signal over time, thus amplifying detection of the probe. Antigen-linked probes allow for antibodies to react with the probe, thus, amplifying the detection of the probe. Similarly for antibody-linked probes.

This invention further provides the above-described methods, wherein the labeled probe comprises an enzyme that produces a detectable product, thereby amplifying detection of the probe.

Examples of enzymes that produce detectable products are phosphatases. Many enzymes, including phosphatases, produce products that are fluorescent or otherwise detectable.

In addition, this invention provides the above-described methods, wherein the labeled probe is radioactive, thereby amplifying detection of the probe.

This invention also provides the above-described methods, wherein the nucleic acid sample obtained from the subject's blood is mRNA and the mRNA is reverse-transcribed to cDNA before amplification.

This invention also provides the above-described methods, wherein the quantifying of step (c) comprises real time polymerase chain reaction.

This invention also provides the above-described methods, wherein the quantifying of step (c) comprises competitive polymerase chain reaction.

This invention also provides the above-described methods, wherein the cancer is breast cancer.

This invention also provides the above-described methods, wherein the cancer is lung cancer.

This invention also provides the above-described methods, wherein the cancer is prostate cancer.

This invention also provides the above-described methods, wherein the cancer is colon cancer.

This invention also provides the above-described methods, wherein the cancer is ovarian cancer.

This invention also provides the above-described methods, wherein the cancer is pancreatic cancer.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

The abbreviations used herein are: SEM, surface-epitope masking; PCTA-1, prostate carcinoma tumor antigen gene-1; BPH, benign prostatic hypertrophy; PIN, prostatic intraepithelial neoplasia; TAAs, tumor associated antigens; RExCS, rapid expression cloning system; MAbs, monoclonal antibodies; 3' UTR, 3' untranslated region; RER, replication error phenotype; LOH, loss of heterozygosity.

An immunological subtraction approach, named surface-epitope masking (SEM), and antibody expression cloning identified a novel gene, prostate carcinoma tumor antigen gene-1 (PCTA-1), with restricted expression in human prostate cancer (Su et al., PNAS, 93: 7252–7257, 1996). Using Northern blotting, RNase protection and RT-PCR we document the specificity of PCTA-1 expression to neoplastic prostate. We also demonstrate that PCTA-1 can be used as a sensitive monitor to detect potentially metastatic cancer cells in the circulation of patients with confirmed metastatic prostate disease. These findings suggest that PCTA-1 may prove useful as a sensitive diagnostic marker for determining prostate cancer progression as indicated by the escape of prostate carcinoma cells from the prostate gland into the bloodstream. PCTA-1 is encoded by a gene located at 1q42–43, an area previously identified as a replication error-type genetic instability locus in human male germ cell tumors. In these contexts, PCTA-1 may play a role in normal germinal cell development and abnormalities in PCTA-1 expression may contribute to the etiology and progression of human prostate cancer.

In the present study we provide definitive evidence for the specificity of PCTA-1 expression in neoplastic prostate. PCTA-1 RNA is detected using Northern blotting, RNase protection and RT-PCR assays in prostate carcinoma cell lines and tissues from patients with cancer, but not in normal prostate or BPH tissues. Data is also presented indicating that PCTA-1 can be detected using RT-PCR when one PCTA-1 expressing cell is diluted in the equivalent of ten million non-PCTA-1 expressing cells. In this context, RT-PCR using PCTA-1 can detect putative metastatic prostate carcinoma cells in the blood of patients with metastatic disease. Chromosome mapping indicates that PCTA-1 is located at 1q42–43, a locus previously reported to be genetically unstable in human male germ cell tumors (14). These findings suggest the intriguing possibility that PCTA-1 may contribute to normal germ cell development and abnormalities in its expression may result in prostate and possibly human germ cell neoplasias.

PCTA-1 expression is prostate carcinoma specific. Previous studies using RT-PCR analysis of PCTA-1 expression in prostate carcinoma cell lines and a small panel of putative normal prostate (4 samples), BPH (4 samples) and prostate carcinoma (7 samples) patient-derived tissue suggest a restricted pattern of PCTA-1 expression to neoplastic prostate (4). In this limited analysis, one putative normal prostate sample and one BPH sample were positive for PCTA-1 expression. However, because the putative normal prostate tissue was obtained from a 60-year old-man, without histological evaluation, it is possible that this tissue may have contained clinically unsuspected prostate disease (4). In the one BPH sample positive for PCTA-1 expression, histological analysis indicated the presence of epithelial atypia consistent with high-grade PIN (4). Although suggestive, these studies do not definitively demonstrate a direct association between PCTA-1 expression and human prostate cancer.

Figure 1B:
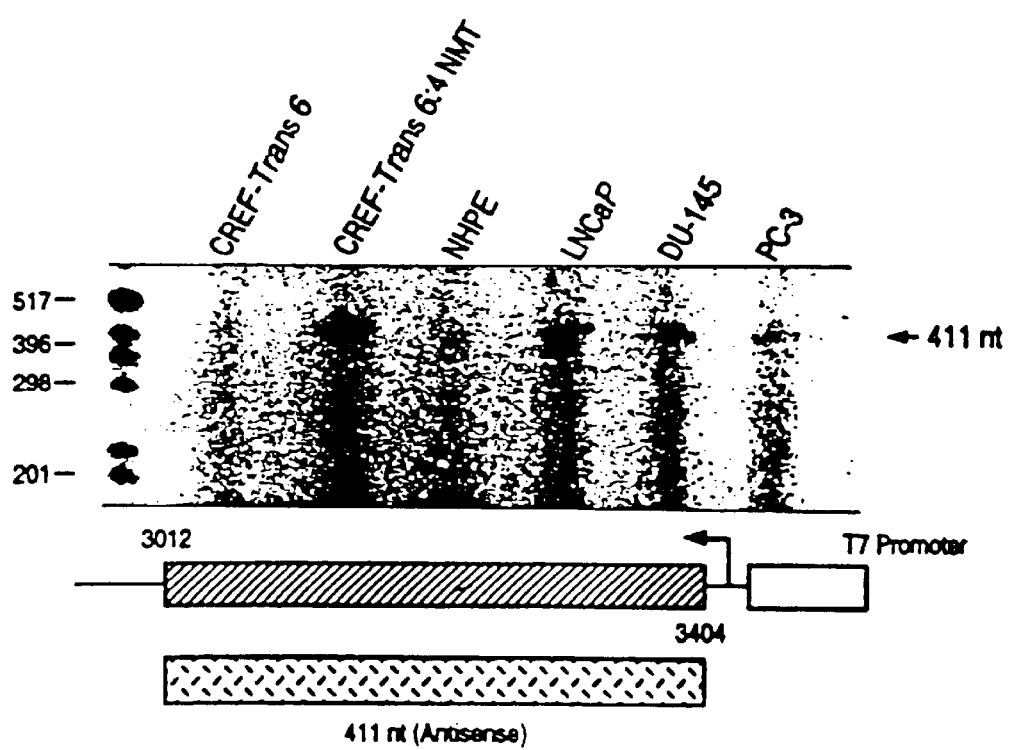
Figure 1C:
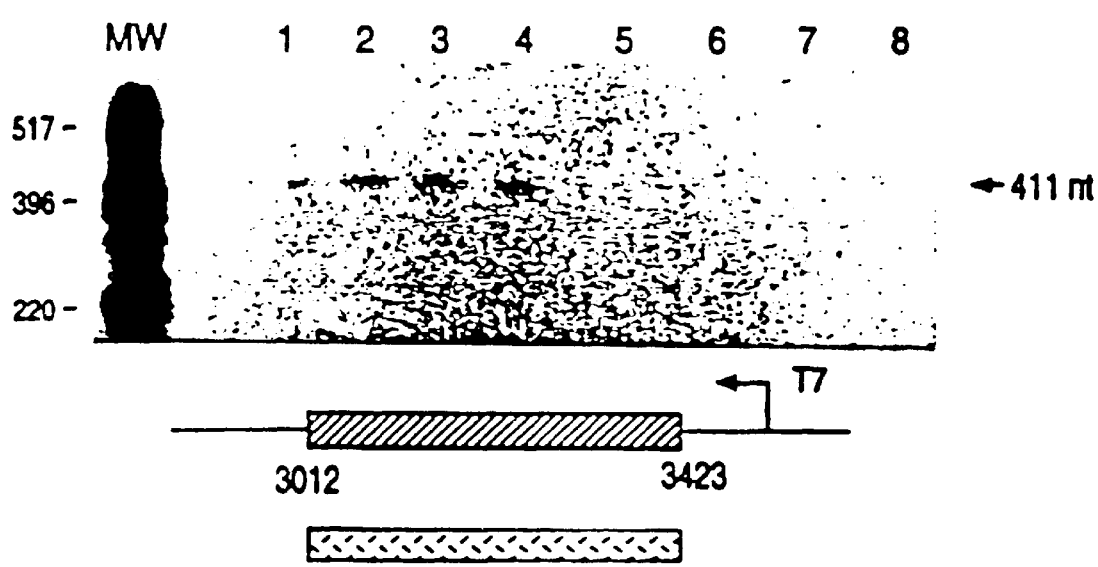

In the present study, three molecular approaches, Northern blotting, RNase protection and RT-PCR, have been used to examine PCTA-1 expression in prostate cell lines and tissue samples from normal prostate, BPH, PIN and carcinoma. Northern blotting indicates the presence of two RNA species (~3.7 and 1.5 kb) in LNCaP-DNA transfected CREF-Trans 6:4 NMT cells and DU-145, LNCaP and PC-3 human prostate carcinoma cell lines (FIG. 1A). In contrast, PCTA-1 expression is not detected in CREF-Trans 6 or NHPE cells. Analysis of tissue RNA demonstrates that PCTA-1 expression is detected, although at low levels (possibly reflecting the heterogeneous nature of the tissue samples), in four of four prostate carcinoma tissues (FIG. 1A). As observed with cultured NHPE cells, no PCTA-1 expression is apparent in normal prostate (2 samples) or in a BPH (1 sample) tissue sample. Similarly, RNase protection assays detect a protected transcript of the appropriate size (411 nt) in CREF-Trans 6:4 NMT, DU-145, LNCaP and PC-3, but not in CREF-Trans 6 or NHPE (FIG. 1B). The level of expression of PCTA-1 is lowest in PC-3, as previously observed using immunofluorescence and immunoprecipitation analyses (4). Examination of four prostate carcinomas, a normal prostate, a low-grade PIN and two BPH tissue samples by RNase protection assays indicate restricted expression of PCTA-1 to neoplastic prostate tissue (FIG. 1C). Although PCTA-1 can be detected in cancer patient tissue samples by Northern blotting and RNase protection assays, these approaches are not ideal for routine screening of clinical materials. The reasons for this include a limited sensitivity of PCTA-1 detection of prostate cancer cells using these approaches (most likely reflecting the small numbers of cancer cells present in the clinical samples analyzed) and the necessity of using relatively large amounts of RNA, 15 to 20 and 5 $\mu$g per assay respectively. This later problem can be particularly prohibitive, especially when only small quantities of clinical material are available. Although the sample size of this study is small, these analyses conclusively demonstrate that PCTA-1 is expressed specifically in prostate carcinoma cell lines and patient-tissues as opposed to normal prostate, BPH or low-grade PIN tissues.

Figure 2A:
FIGS. 2A and 2B RT-PCR detects PCTA-1 expression in prostate carcinoma tissues and in diluted cell culture samples.

RT-PCR has revolutionized the analysis of clinical samples for detecting expression of small quantities of a specific target gene sequence. On the basis of our initial analysis (4), this approach appeared ideal for testing the hypothesis that PCTA-1 expression is a defining event in prostate cancer development. To investigate this possibility tissue samples representing normal prostate, BPH, PIN and prostate carcinoma were analyzed for PCTA-1 expression. Expression was apparent in prostate carcinoma tissue samples (12 of 12), but not in normal prostate (0 of 6), BPH (0 of 7) and low grade and focal PIN (0 of 4) (FIGS. 2A and data not shown). The PCTA-1 positive prostate carcinoma tissues included samples with as little as 5% tumor with PIN to as much as 20% tumor. These findings confirm the specificity of RT-PCR for detecting PCTA-1 expression in prostate cancer tissue samples. Since these assays require only small quantities of RNA, i.e. $\leq$1 $\mu$g, and they are highly sensitive in detecting small number of cancer cells in a great excess of normal cells, RT-PCR of PCTA-1 will prove valuable as a diagnostic approach for accurately detecting prostate cancer in tissue that cannot be achieved using RT-PCR of PSA, since expression occurs in normal prostate, BPH, PIN and prostate carcinoma (4).

Figure 2B:
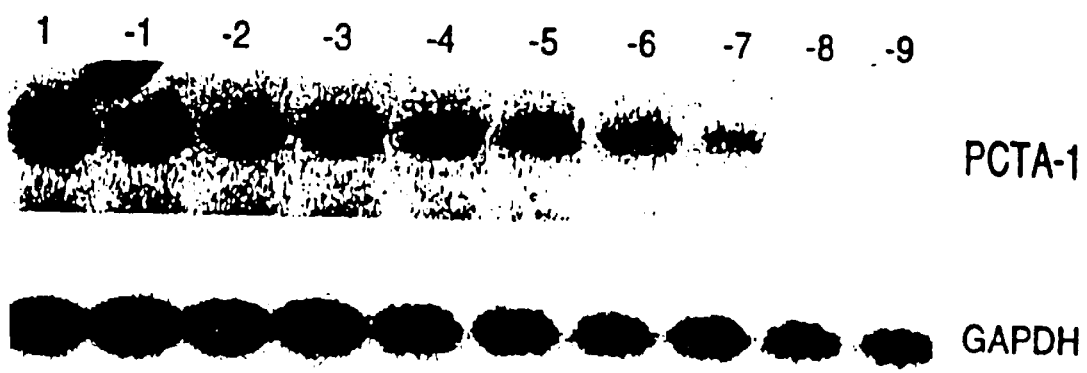

PCTA-1 expression is detected in the blood of patients with metastatic prostate cancer. To define potential applications for using RT-PCR of PCTA-1 in staging and monitoring prostate cancer progression, PCTA-1 expressing CREF-Trans 6:4 NMT (DU-145 or LNCaP) cells were serially diluted with non-PCTA-1 expressing CREF-Trans 6 cells; total RNA was isolated, and samples were compared by RT-PCR (FIG. 2B and data not shown). Using primers designed in the 3' UTR of PCTA-1, a positive PCTA-1-specific amplified fragment (411 nt) is present when 1 CREF-Trans 6:4 NMT (DU-145 or LNCaP) cell is diluted in $10^7$ CREF-Trans 6 cells (FIG. 2B and data not shown). This level of sensitivity exceeds that obtained when performing similar RT-PCR assays with LNCaP cells diluted in CREF-Trans 6 cells and monitoring PSA (sensitivity of 1 in $10^6$) or prostate-specific membrane antigen (sensitivity of 1 in $10^5$) (6). However, the sensitivity of PCTA-1 is 10-fold less than obtained when performing RT-PCR with the same samples and monitoring for expression of a novel oncogene overexpressed in prostate carcinoma cells, prostate tumor inducing gene-1 (PTI-1) (sensitivity of 1 in $10^8$) (3,6,19). These results demonstrate that PCTA-1 is a sensitive detector of human prostate carcinoma cells, exceeding the sensitivity of PSA and PSM.

Figure 3A:
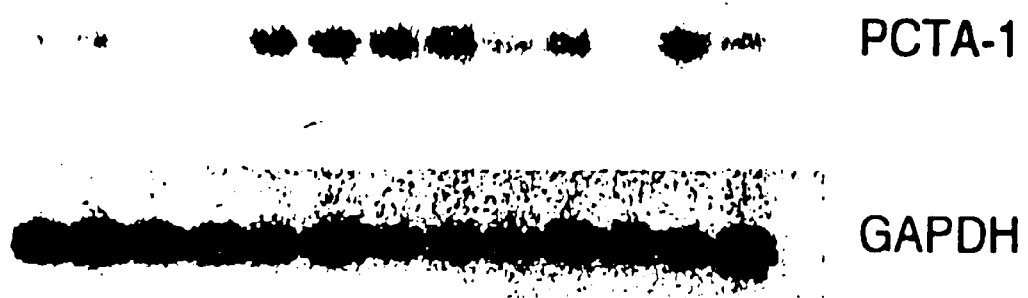
FIGS. 3A and 3B RT-PCR detects PCTA-1 expression in blood samples from patients with metastatic prostate cancer. Blood RNAs were subjected to RT-PCR using PCTA-1 and GAPDH specific primer pairs (4). PCR-amplified products generated using a PCTA-1 3' UTR or a GAPDH primer pair (4) were Southern blotted and probed with a $^{32}$P-labeled DNA fragment of PCTA-1 or GAPDH, respectively.
Figure 3B:
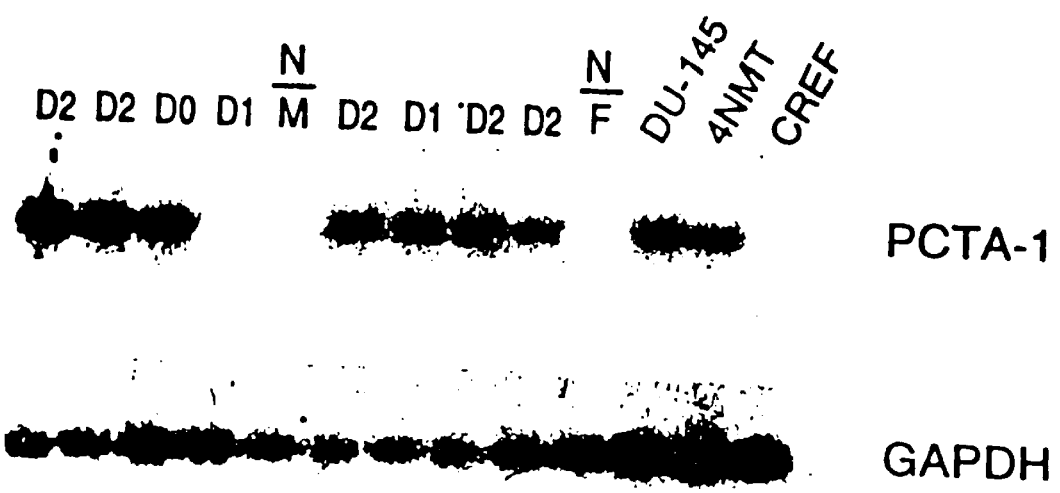

The ability of PCTA-1 to detect 1 expressing cell in a background of $10^7$ non-expressing cells suggested that it might be possible to use RT-PCR of PCTA-1 as a sensitive screening test for detecting potential metastatic prostate cancer cells in the bloodstream of prostate cancer patients. To directly address this possibility, blood RNA samples were obtained from 19 patients in clinical stage D (including 12 D2, 5 D1 and 2 D0) with PSA serum levels ranging from 0.2 to 1912.3 ng/ml (data not shown). All of these D stage patients with progressive disease were positive for PCTA-1 expression (FIGS. 3A and 3B). Although RT-PCR is not quantitative, 3 of 5 D1 stage patient samples generated lower hybridization signals (relative to GAPDH) than corresponding D2 patient samples. Similarly, 2 of 2 D0 patient blood samples were positive for PCTA-1 expression, with 1 of 2 samples generating only a weak hybridization signal. In contrast, two RNA blood samples from normal males and one RNA blood sample from a normal woman volunteer were negative for PCTA-1 expression (FIGS. 3A and 3B). Similarly, one blood RNA sample from a patient in clinical stage C was also negative for PCTA-1 expression. Although these results require further validation with a larger number of clinical samples from patients with different stages of prostate cancer, the present studies provide supportive evidence suggesting that RT-PCR of PCTA-1 may prove amenable for monitoring prostate cancer progression in patients.

Figure 4A:
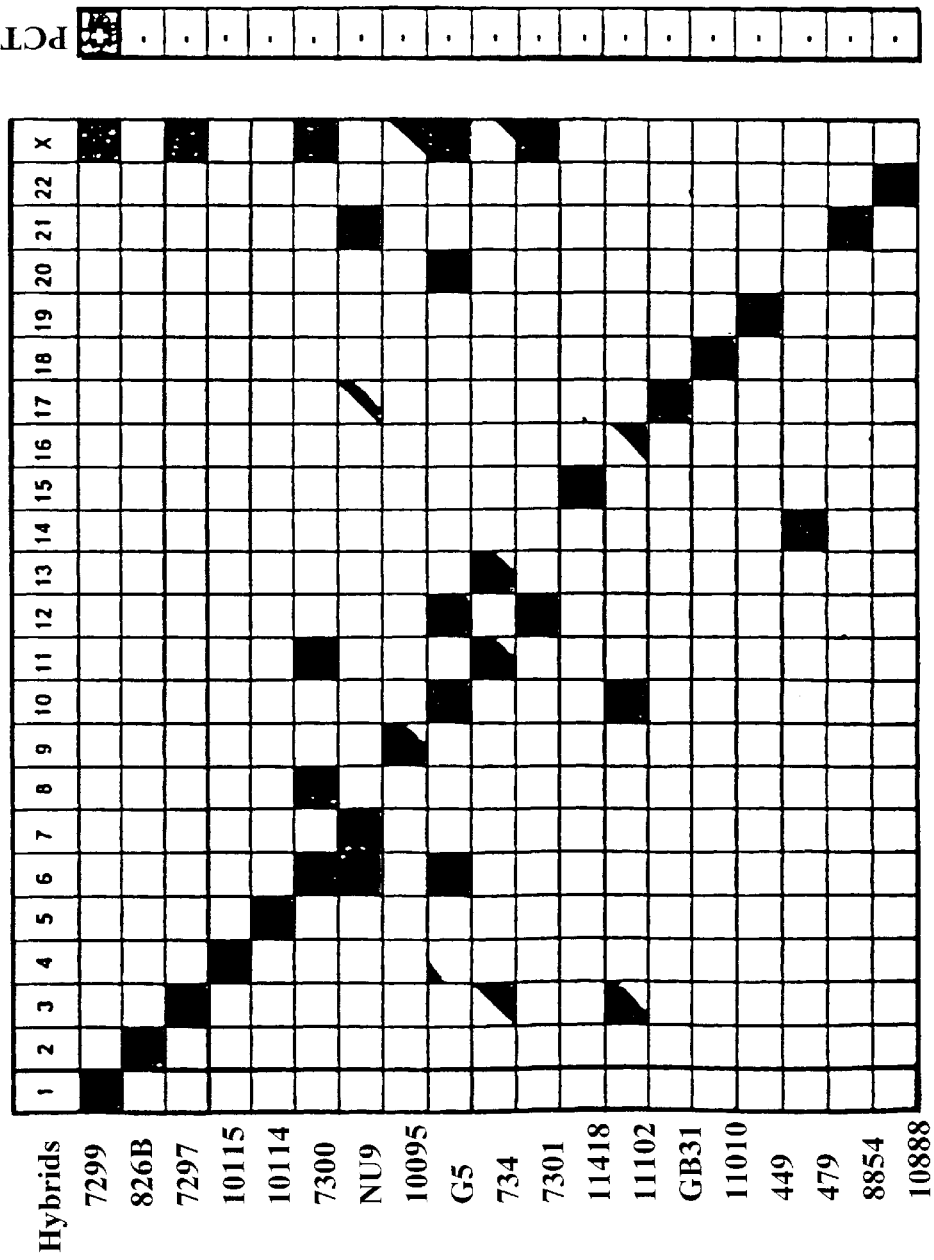
FIG. 4A Presence of the PCTA-1 gene in a panel of 19 rodent-human hybrids. A fully shaded box indicates that the hybrid named in the left column contains the chromosome indicated in the upper row; a box shaded in the lower right indicates the presence of the long arm of the chromosome (or part of the long arm represented by a smaller fraction of stippling); a box shaded in the upper left indicates the presence of the short arm (or partial short arm) of the chromosome; an unshaded box indicates the absence of the chromosome listed above the column. The column for chromosome 1 is outlined in bold and stippled to highlight correlation of presence of the PCTA-1 gene. The pattern of retention of the PCTA-1 locus in the panel is shown to the right of the figure where presence of the locus in a hybrid is indicated by a stippled box with a plus sign and absence of the locus is indicated by an open box enclosing a minus sign.
Figure 4B:
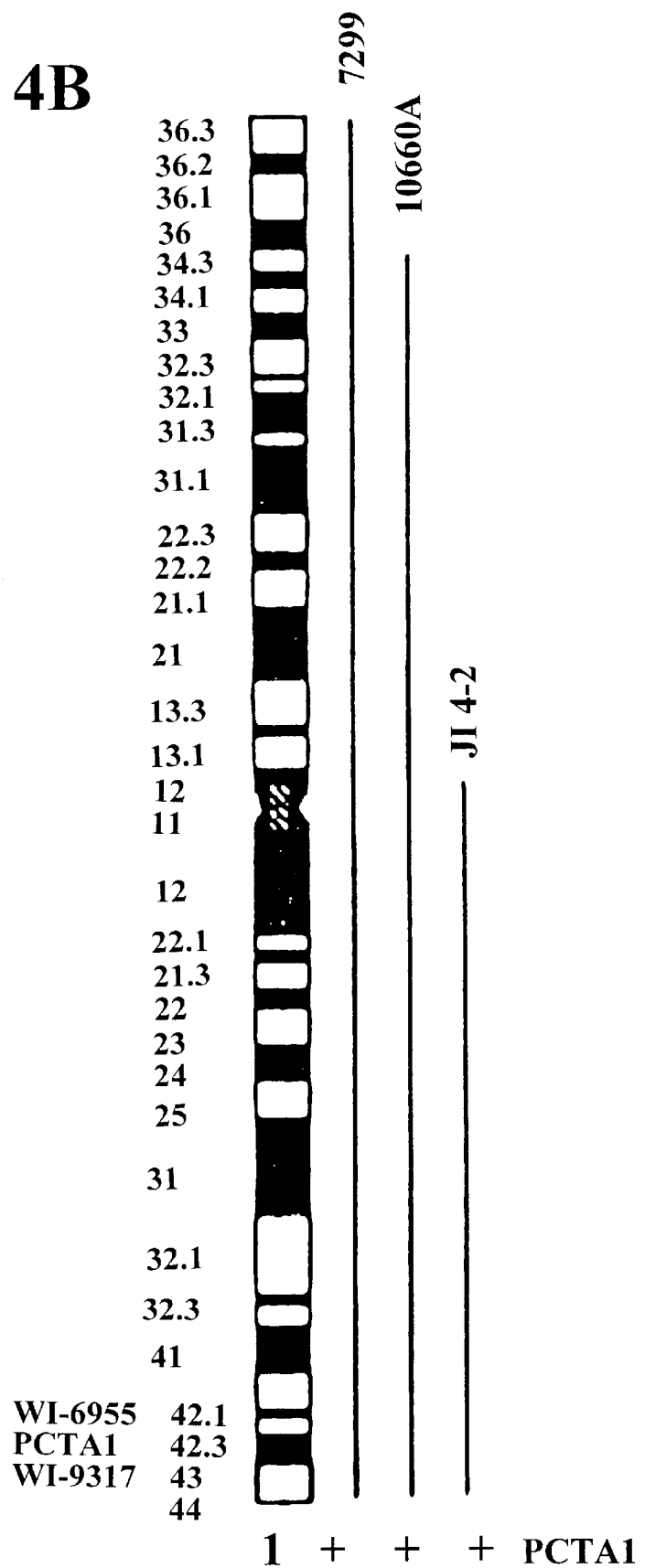
FIG. 4B Regional localization of the PCTA-1 locus to 1q. The portion of chromosome 1 present in specific hybrids is represented by the solid lines to the right of the chromosome 1 idiogram. These hybrids were tested for presence of the PCTA-1 gene by PCR amplification, and presence or absence of the gene is indicated below the lines representing specific hybrids. The line to the left of the chromosome 1 idiogram shows the regional localization of the PCTA-1 gene as determined by linkage to other markers (also shown) in the Stanford and/or Whitehead rhservers.

The human PCTA-1 gene maps to chromosome 1q42–43. Important information relative to the potential function and/or relationship between a specific cDNA and a disease state can be obtained by defining chromosomal localization of the gene. To address this question, DNA from a panel of rodent-human hybrids, together carrying most human chromosome regions, were tested for presence of the PCTA-1 locus by PCR amplification. Hybrid DNAs were scored positive if they exhibited a 177 bp PCTA-1 human specific product. Hybrids retaining chromosome region 1q in common had the PCTA-1 specific product; those without 1q did not have a human PCTA-1 product, as summarized in FIG. 4A and illustrated in FIG. 4B. To further refine the localization of PCTA-1, the Stanford RH panel (Research Genetics) was tested by PCR-amplification for the PCTA-1 fragment. The scoring data was submitted to the Stanford rhserver (rhserver@shgc.stanford.edu) and results calculated by the server showed linkage to two markers (with LOD score greater than 6). D1S235 and D1S446 were linked to PCTA-1 at distances of 16.98 cR-8000 and 33.23 cR-8000, respectively. This data was confirmed after testing the Genebridge radiation hybrid DNAs (Research Genetics).

The WICGR mapping server (www.genome.wi.mit.edu/cgi-bin/contig/rhmapper.pl) found very close linkage to WI-9317 (DIS2421) and WI-6955 (DIS2383). Thus, PCTA-1 maps to the chromosome region 1q42–43, where these linked markers have been localized (20).

EXPERIMENTAL DISCUSSION

Using a combination of approaches, including REXCS (3) and SEM (4), a novel galectin, PCTA-1, has been identified that displays differential expression in prostate cancer cells versus normal prostate cells (3,4,6). In the present study several molecular approaches, including Northern blotting, RNase protection and RT-PCR, have been used to document restricted expression of PCTA-1 to neoplastic prostate. Concurrence of results by three independent methods of RNA detection validates the use of RT-PCR as the method of choice, particularly in a scenario of availability of limiting RNA samples. Serial-dilution experiments demonstrate that PCTA-1 can be detected when 1 expressing cell is diluted in $10^7$ non-expressing cells. An analysis of blood RNAs by RT-PCR further document that monitoring PCTA-1 expression represents a sensitive indicator of potentially metastatic prostate cancer cells in the blood stream of cancer patients. The restricted expression of PCTA-1 to neoplastic prostate and the ability to detect expression of this gene in blood RNAs from patients with confirmed and suspected metastatic disease suggest that PCTA-1 monitoring may prove valuable for diagnostically staging prostate cancer progression as indicated by the presence of prostate carcinoma cells in the circulation. In this context, determining PCTA-1 expression in blood RNAs represents a sensitive non-invasive methodology for determining extraprostatic disease in patients prior to surgery, routine staging of prostate cancer progression, and evaluating patients' response to chemotherapy and radiation therapy.

A number of chromosomal abnormalities are present in cells from human prostate cancer (21–25). These include, duplication of sequences located on the distal arm of chromosome 8 (21) and the loss of DNA sequences from the short arm of chromosomes 8 and 11 and the long arm of chromosome 13 (22,23). Recent studies using linkage analysis with prostate cancer-prone families provides evidence for a region of the long arm of chromosome 1 (1q24–25) as the location of a gene(s) representing a potential site for predisposition to prostate cancer (24,25). This study suggests that chromosome 1, specifically 1q, previously considered not to be an important region in prostate cancer, may in fact be a major susceptibility locus for this disease. In this context, the localization of PCTA-1 to chromosome 1q, specifically 1q42–43, suggests that chromosome 1 may also contain a gene that directly contributes to the cancerous potential of prostate cancer cells.

The RER phenotype, recognized as microsatellite sequence alterations, has been suggested to be associated with cancer development, specifically hereditary nonpolyposis colorectal cancer and several types of sporadic tumors (26). Microsatellite instability reflects a pathway in the development of tumors that can be distinguished from a direct loss of tumor suppressor gene function that is distinctive of many tumor suppressor genes. A high frequency of (CA)n sequence instability is evident in several types of sporadic human tumors, including colorectal (12–28%) (27), endometrial (17%) (28), pancreatic (67%) (29), gastric (22.7–39%) (24), prostate (37.5%) (30), breast (10.6%) (31) and germ cell tumor (18.2%) (14). In the case of germ cell tumors, an ~18.2% RER type genetic instability occurs at 1q42–43 (14), the location of PCTA-1. It is possible that the genetic instability at 1q42–43 modifies PCTA-1 expression and may mediate or correlate with the development of germ cell tumors. This hypothesis is currently being tested experimentally.

The effective uses of MAbs as diagnostic and therapeutic reagents in cancer require that they embody the appropriate selective specificity toward tumor cells. Surface molecules represent potentially useful targets for MAb-based therapeutics (32–34). Production of MAbs reacting with antigens present on the surface of tumor cells, but displaying restricted expression on normal cells, is often a difficult and inefficient process. The SEM procedure (7,8) has been developed that in principal can obviate many of the limitations preventing efficient MAb development toward molecules expressed on the cell surface. The SEM approach has been successfully used for a number of applications resulting in the production of MAbs specific for surface expressed molecules with known and unknown functions (4,7,8). We have successfully used SEM in combination with RExCS to develop MAbs reacting with antigens expressed preferentially on the surface of human prostate and breast cancer (4,7,8 and unpublished data). Moreover, repeated injection of the SEM-derived Pro 1.5 MAb into athymic nude mice containing established DU-145 human prostate tumor xenografts inhibits tumor growth and even results in complete tumor remission in specific animals. These provocative findings demonstrate a direct effect of Pro 1.5 MAbs on the growth and progression of human prostate cancers in vivo. The SEM procedure should prove extremely useful in producing MAbs and identifying genes associated with important cellular processes, including growth control, differentiation, senescence, immunologic recognition, tumorigenesis, metastasis, atypical multidrug resistance and autoimmune diseases.

In summary, SEM in combination with RExCS is an extremely sensitive and efficient technology to develop MAbs and for cloning genes expressed differentially in cancer versus normal tissue. The identification of PCTA-1 as a gene associated with human prostate cancer development and evolution provides proof of principle for these applications in identifying a potentially relevant gene in human prostate cancer. The demonstration that PCTA-1 is located on the long arm of chromosome 1 also indicates that this chromosomal region may contain genes responsible for both the susceptibility to prostate cancer and a gene that determines the aggressiveness of prostate cancers.

MATERIALS AND METHODS

Cell Lines, Tumor Tissue and Blood Samples. The following cell types were used: early passage normal human prostate epithelial cells (NHPE, passage number <12), prostate carcinoma cells (DU-145, LNCaP and PC-3), cloned rat embryo fibroblast cells (CREF-Trans 6) and nude mouse tumor-derived CREF-Trans 6 cells transfected with LNCaP DNA (CREF-Trans 6:4 NMT). NHPE cells were grown in defined serum-free medium provided by Clonetics (San Diego, Calif.). The different cell lines were grown in DMEM supplemented with 5% (rodent cells) or 10% (human cells) fetal bovine serum at 37° C. in a 95% air/5% $CO_2$-humidified incubator. Tissue samples from normal prostates, patients with BPH, low-grade PIN, high-grade PIN and carcinoma were obtained during surgery or from autopsies performed at Columbia Presbyterian Medical Center (Dr. Carl A. Olsson, Department of Urology, Columbia University College of Physicians and Surgeons, New York, N.Y.) and from the Cooperative Human Tumor Network (CHTN). Blood RNAs used in this study were obtained from patients at Columbia-Presbyterian Medical Center and from Dr. Gerald Murphy (Pacific Northwest Cancer Foundation, Seattle, Wash.). Tissue and blood samples were obtained with informed consent of each patient using protocols approved by the Institutional Review Boards. Sample analysis included blood samples from patients with D stage disease, a patient with C stage disease and normal males and a female.

RNA Isolation from Human Prostate Cells, Tissues and Blood Samples. Total RNA was isolated from human normal prostate, BPH, PIN and carcinoma tissue using the TRizol reagent (Life Technologies) as described previously (3). Briefly, tissue samples were frozen in liquid nitrogen and homogenized into powder (3,4). To each gram of tissue, 10 ml of TRizol was added and mixed thoroughly followed by incubation at room temperature for 5 min. To each ml of TRizol added, 0.2 ml of chloroform was added and the reactants were thoroughly mixed. The tubes were centrifuged at 12,000×g for 15 min and the aqueous phase was transferred to a fresh tube. RNA was precipitated with iso-propyl alcohol and washed with 75% alcohol. After drying, RNA was dissolved in RNase free water.

Northern blotting and RNase Protection Assays. Total cellular RNA was isolated by guanidinium/phenol extraction method and Northern blotting was performed as described (3,15). Fifteen μg of RNA were denatured with glyoxal/DMSO and electrophoresed in 1% agarose gels, transferred to nylon membranes and hybridized sequentially with $^{32}$P-labeled PCTA-1 (an ~600 nt 3' UTR; nt 1437 to nt 2014) and GAPDH probes (3,15). Following hybridization, the filters were washed and exposed for autoradiography. RNase protection assays were performed using the Ambion Ribonuclease Protection Assay Kit (Ambion, Tex.) as described previously (16). Briefly, a PCTA-1 antisense RNA probe was made by in vitro transcription and labeled with $^{32}$P-UTP, hybridized with total cellular RNA and digested with a mixture of RNase A and RNase $T_1$. After electrophoresis in 6% polyacrylamide gels and autoradiographic exposure a protected RNA fragment appeared as a distinct band of predicted (411 nt) molecular size.

Determination of PCR Sensitivity and RT-PCR Assays. Sensitivity of PCTA-1 detection using RT-PCR was determined as described previously (6). RNA was isolated from CREF-Trans 6:4 NMT, DU-145 or LNCaP cells and from mixtures of CREF-Trans 6:4 NMT, DU-145 or LNCaP and CREF-Trans 6 cells ranging from 1:1 to 1:1,000,000,000 as described previously (3). RT-PCR of PCTA-1 was performed using two 20-mers with the sequences 5'-AAGCTGACGCCTCATTTGCA-3' SEQ ID NO:1 and 5'-AACCACCAATGGAACTGGGT-3' SEQ ID NO:2 and PCR of GAPDH was performed using a pair of primers with the sequences 5'-TCTTACTCCTTGGAGGCCATG-3' SEQ ID NO:5 and 5'-CGTCTTCACCACCATGGAGAA-3' SEQ ID NO:6 (3). The PCR-amplified products were blotted on nylon membranes and probed with a $^{32}$P-labeled DNA fragment of PCTA-1 or GAPDH, respectively. The CREF-Trans 6 cell line was chosen to dilute CREF-Trans 6:4 NMT, DU-145 and LNCaP cells because this cell line does not express PCTA-1 (4).

Chromosomal Localization. Rodent-human hybrids. Many of the hybrids used in this study are available through the Human Genetic Mutant Repository (HGMCR Coriell Institute, Camden, N.J.) or were described previously (17). Stanford and Genebridge radiation hybrid (RH) mapping panels (18,19) were purchased from Research Genetics (Huntsville, Ala.). PCR amplification. The oligonucleotides for generating PCR products were selected using the computer program Oligo 4.0 (National Biosciences). Primers used to amplify a 177 bp PCTA-1 product were: PCTAF, 5'-AATGGCTTCTGTGATACT-3' SEQ ID NO:3 and PCTAR, 5'-GGCTATAAGTGTTGCTGC-3' SEQ ID NO:4. PCR reactions were carried out in a final volume of 12.5 μl with 100 ng of template, 20 ng primers, 10 mM tris-HCl pH 8.3, 50 mM KCl, 0.1 mg/ml gelatin, 15 mM MgCl2, 200 μM NTPs and 0.5 U Taq polymerase. Amplifications were performed in a Perkin-Elmer Cetus 9600 thermal cycler for 30 cycles of 94° C. for 30s, 58° C. for 30s and 72° C. for 30s. The PCR products were visualized in ethidium bromide stained 1.5% agarose gels. The amplification product of the gene was sequenced to ensure its identity. The product was purified with Qiagen PCR purification kit, and 1 ng of DNA and 20 ng specific primer used with the Taq Dye Deoxy Terminator Cycle Sequencing Kit (ABI). The reaction products were electrophoresed and recorded on the 377 DNA sequencer (ABI).

REFERENCES

1. Murphy, G. P., Lawrence, W., Jr., and Lenhard, R. E., Jr. American Cancer Society Textbook of Clinical Oncology, 2nd Ed., Amer. Cancer Soc., Atlanta, Ga., 1995.
2. Su, Z.-z., Olsson, C. A., Zimmer, S. G., and Fisher, P. B. Transfer of a dominant-acting tumor-inducing oncogene from human prostatic carcinoma cells to cloned rat embryo fibroblast cells by DNA-transfection. Anticancer Res., 12: 297–304, 1992.
3. Shen, R., Su, Z.-z., Olsson, C. A., and Fisher, P. B. Identification of the human prostatic carcinoma oncogene PTI-1 by rapid expression cloning and differential RNA display. Proc. Natl. Acad. Sci. U.S.A., 92: 6778–6782, 1995.
4. Su, Z.-z., Lin, J., Shen, R., Fisher, P. E., Goldstein, N. I., and Fisher, P. B. Surface-epitope masking and expression cloning identifies the human prostate carcinoma tumor antigen gene PCTA-1 a member of the galectin gene family. Proc. Natl. Acad. Sci. U.S.A., 93: 7252–7257, 1996.
5. Wang, F.-L., Wang, Y., Wong, W-K., Liu, Y., Addivinola, J., Liang, P., Chen, L. B., Kantoff, P. W., and Pardee, A. B. Two differentially expressed genes in normal human prostate tissue and in carcinoma. Cancer Res., 56: 3634–3637, 1996.
6. Sun, Y., Lin, J., Katz, A. E., and Fisher, P. B. Human prostatic carcinoma oncogene PTI-1 is expressed in human tumor cell lines and prostate carcinoma patient blood samples. Cancer Res., 57: 18–23, 1997.
7. Shen, R., Su, Z.-z., Olsson, C. A., Goldstein, N. I., and Fisher, P. B. Surface-epitope masking: a strategy for the development of monoclonal antibodies specific for molecules expressed on the cell surface. J. Natl. Cancer Inst., 86: 91–98, 1994.
8. Fisher, P. B. A new technology for preparing monoclonal antibodies to molecules expressed on the cell surface. Pharmaceutical Tech., 19 (9): 42–48, 1995.
9. Drickamer, K., and Taylor, M. E. Biology of animal lectins. Annu. Rev. Cell Biol., 9: 237–264, 1993.
10. Barondes, S. H., Cooper, D. N. W., Gitt, M. A., and Leffler, H. Galectins: structure and function of a large family of animal lectins. J. Biol. Chem., 269: 20807–20810, 1994.
11. Raz, A., and Lotan, R. Endogenous galactoside-binding lectins: a new class of functional tumor cell surface molecules related to metastasis. Cancer Metastasis Rev., 6: 433–452, 1987.
12. Liotta, L. A., Steeg, P. G., and Stetler-Stevenson, W. G. Cancer metastasis and angiogenesis: an imbalance of positive and negative regulation. Cell, 64: 327–336, 1991.

13. Su, Z.-z., Yemul, S., Estabrook, A., Friedman, R. M., Zimmer, S. G., and Fisher, P. B. Transcriptional switching model for the regulation of tumorigenesis and metastasis by the Ha-ras oncogene: transcriptional changes in the Ha-ras tumor suppressor gene lysyl oxidase. Intl. J. Oncology, 7: 1279–1284, 1995.
14. Murty, V. V. V. S., Li, R-G., Mathew, S., Reuter, V. E., Bronson, D. L., Bosl, G. J., and Chaganti, R. S.K. Replication error-type genetic instability at 1q42–43 in human male germ cell tumors. Cancer Res., 54: 3983–3985, 1994.
15. Jiang, H., and Fisher, P. B. Use of a sensitive and efficient subtraction hybridization protocol for the identification of genes differentially regulated during the induction of differentiation in human melanoma cells. Mol. Cell. Different. 1 (3): 285–299, 1993
16. Su, Z.-z., Goldstein, N. I., and Fisher, P. B. Antisense inhibition of the PTI-1 oncogene reverses cancer phenotypes. Proc. Natl. Acad. Sci. USA, 90: 1764–1769, 1998.
17. Feinstein, E., Druck, T., Kastury, K., Berissi, H., Goodart, S. A., Overhauser, J., Kimchi, A. and Huebner, K. Assignment of DAP1 and DAPK-genes that positively mediate programmed cell death triggered by IFN-γ-to chromosome regions 5p12.2 and 9q34.1, respectively. Genomics, 29: 305–307, 1995.
18. Cox, D. R., Burmeister, M., Price, E. R., Kim, S., and Myers, R. M. Radiation hybrid mapping: A somatic cell genetic method for constructing high-resolution maps of mammalian chromosomes. Science, 250: 245–250, 1990.
19. Walter, M. A., Spillet, D. J., Thomas, P., Weissenbach, J., and Goodfellow, P. N. A method for constructing radiation hybrid maps of whole genomes. Nature Genet., 7: 22–28, 1994.
20. Chumakov, I. M., et al. The Genome Directory- A YAC contig map of the human genome. Nature, 377 (Supplement): 175–297, 1995.
21. Visakorpi, T., Kallioniemi, A. H., Syvanen, A. C., Hyytinen, E. R., Karhu, R., Tammela, T., Isola, J. J., and Kallioniemi, O. P. Genetic changes in primary and recurrent prostate cancer by comparative genomic hybridization. Cancer Res., 55: 342–347, 1995.
22. Cher, M. L., Bova, G. S., Moore, D. H., Small, E. J., Carroll, P. R., Pin, S. S., Epstein, J. I., Isaacs, W. B., and Jensen, R. H. Genetic alterations in untreated metastases and androgen-independent prostate cancer detected by comparative genomic hybridization and allelotyping. Cancer Res., 56: 3091–3102, 1996.
23. Emmert-Buck, M. R., Vocke, C. D., Pozatti, R. O., Duray, P. H., Jennings, S. B., Florence, C. D., Zhuang, Z., Bostwick, D. G., Liotta, L. A., and Linehan, W. M. Allelic loss on chromosome 8p12–21 in microdissected prostatic intraepithelial neoplasia. Cancer Res., 55: 2959–2962, 1995.
24. Smith, J. R., Freije, D., Carpten, J. D., Gronberg, H., Xu, J., Issacs, S. D., Brownstein, M. K., Bova, G. S., Guo, H., Bujnovszky, Nusskern, D. R., Damber, J-E., Bergh, A., Emanuelsson, M., Kallioniemi, O. P., Walker-Daniels, J., Bailey-Wilson, J. E., Beaty, T. H., Meyers, D. A., Walsch, P. C., Collins, F. S., Trent, J. M., and Issacs, W. B. Major susceptibility locus for prostate cancer on chromosome 1 suggested by a genome-wide search. Science (Washington D.C.), 274: 1371–1374,1996.
25. Gronberg, H., Xu, J., Smith, J. R., Carpten, J. D., Issacs, S. D., Freije, D., Bova, G. S., Walsh, P. C., Collins, F. S., Trent, J. M., Meyers, D. A., and Issacs, W. B. Early age at diagnosis in families providing evidence of linkage to the hereditary prostate cancer locus (HPC1) on chromosome 1. Cancer Res., 57: 4707–4709, 1997.
26. Peltomaki, P., Aaltonen, L. A., Sistonen, P., Pylkkanen, L., Mecklin, J-P., Jarvinen, H., Green, J. S., Weber, J. L., Leach, F. S., Petersen, G. M., Hamilton, S. R., de la Chapelle, A., and Vogelstein, B. Genetic mapping of a locus predisposing to human colorectal cancer. Science (Washington D.C.), 260: 810–812, 1993.
27. Aalto nen, L. A., Peltomaki, P., Leach, F. S., Sistonen, P., Pylkkanen, L., Mecklin, J-P., Jarvinen, H., Powell, S. M., Jen, J., Hamilton, S. R., Petersen, G. M., Kinzler, K. W., Vogelstein, B., and de la Chapelle, A. Clues to the pathogenesis of familial colorectal cancer. Science (Washington D.C.), 260: 812–816, 1993.
28. Risinger, J. I., Berchuck, A., Kohler, M. F., Watson, P., Lynch, H. T., and Boyd, J. Genetic instability of microsatellites in endometrial carcinoma. Cancer Res., 53: 5100–5103, 1993.
29. Han, H-J, Yanagisawa, A ., Kato, Y., Park, J-G., and Nakamura, Y. Genetic instability in pancreatic cancer and poorly differentiated type of gastric cancer. Cancer Res., 53: 5087–5089, 1993.
30. Uchida, T., Wada, C., Wang, C., Ishida, H., Egawa, S., Yokoyama, E., Ohtani, H., and Koshiba, K. Microsatellite instability in prostate cancer. Oncogene, 10: 1019–1022, 1995.
31. Wo oster, R., Cleton-Jansen, A-M., Collins, N., Mangion, J., Cornelis, R. S., Cooper, C. S., Custerson, B. A., Ponder, B. A. J., von Deimling, A., Wiestler, 0. D., Cornelisse, C. J., Devilee, P., and Stratton, M. R. Instability of short tandem repeats (microsatellites) in human cancers. Nat. Genet., 6: 152–156, 1994.
32. Greiner, J. W., Schlom, J., Pestka, S., Langer, J. A., Giacomini, P., Kusama, M., Ferrone, S., and Fisher, P. B. Modulation of tumor associated antigen expression and shedding by recombinant human leukocyte and fibroblast interferons. P harmacology and Therapeutics, 31: 209–236, 1985.
33. Waldman, T. A. Monoclonal antibodies in diagnosis and therapy. Science (Washington D.C.), 252: 1657–1662, 1991.
34. Leon, J. A., Goldstein, N. I., and Fisher, P. B. New approaches for the development and application of monoclonal antibodies for the diagnosis and therapy of human cancer. Pharmacol. Therap., 61: 237–278, 1994.

What is claimed is:

1. A method of detecting metastatic prostate cancer cells in a human subject's blood which comprises detecting in RNA obtained from cells present in the subject's blood, RNA which encodes prostate carcinoma tumor antigen-1, wherein the presence of said RNA which encodes prostate carcinoma tumor antigen-1 is indicative of the presence of metastatic prostate cancer cells in the human subject's blood.

2. A method of detecting metastatic prostate cancer cells in a human subject's blood, comprising:
   a. obtaining RNA from cells present in the subject's blood;
   b. admixing the RNA obtained in step (a) with two nucleic acid primers consisting of the sequence 5'-AAGCTGACGCCTCATTTGCA-3' (Seq. ID 1) and 5'-AACCACCAATGGAACTGGGT-3' (Seq. ID 2) and subjecting the mixture to a polymerase chain reaction to produce a polymerase chain reaction amplified product;
   c. contacting the amplified product from step (b) with a labeled probe which specifically hybridizes with nucleic acid encoding prostate carcinoma tumor antigen-1wherein specifically hybridized probe produces a signal; and
   d. detecting the presence of said signal, as indicative of the presence of nucleic acid encoding prostate carcinoma tumor antigen-1, wherein the presence of said nucleic acid encoding prostate carcinoma tumor antigen-1 is indicative of the presence of metastatic prostate cancer cells in the human subject's blood.

3. A method of detecting metastatic prostate cancer cells in a human subject's blood, comprising:
   a. obtaining RNA from cells present in the subject's blood;
   b. admixing the RNA obtained in step (a) with two nucleic acid primers consisting of the sequence 5'-AATGGCTTCTGTGATACT-3' (Seq. ID 3) and 5'-GGCTATAAGTGTTGCTGC-3' (Seq ID 4) and subjecting the mixture to a polymerase chain reaction to produce a polymerase chain reaction amplified product;
   c. contacting the amplified product from step (b) with a labeled probe which specifically hybridizes with nucleic acid encoding prostate carcinoma tumor antigen-1 wherein specifically hybridized probe produces a signal; and
   d. detecting the presence of said signal as indicative of the presence of nucleic acid encoding prostate carcinoma tumor antigen-1, wherein the presence of said nucleic acid encoding prostate carcinoma tumor antigen-1 is indicative of the presence of metastatic prostate cancer cells in the human subject's blood.

4. The method of claim 2, wherein the RNA obtained from the subject's blood is total cellular RNA wherein the total cellular RNA is reverse-transcribed to cDNA before amplification.

* * * * *